(12) United States Patent
Hurschmann et al.

(10) Patent No.: US 6,364,913 B1
(45) Date of Patent: *Apr. 2, 2002

(54) AGENT AND PROCESS FOR DYEING AND TINTING KERATINOUS FIBRES

(75) Inventors: Brigitta Hurschmann, Remscheid; Detlef Hollenberg, Erkrath, both of (DE)

(73) Assignee: Henkel Kommanditgesellschaft auf Aktien, Duesseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,741

(22) PCT Filed: May 5, 1997

(86) PCT No.: PCT/EP97/02280

§ 371 Date: Nov. 13, 1998

§ 102(e) Date: Nov. 13, 1998

(87) PCT Pub. No.: WO97/42932

PCT Pub. Date: Nov. 20, 1997

(30) Foreign Application Priority Data

May 13, 1996 (DE) .......................... 196 19 071

(51) Int. Cl.⁷ ................................ A61E 7/13
(52) U.S. Cl. ................... 8/428; 8/405; 8/414; 8/415; 8/426; 8/428; 8/552; 8/578
(58) Field of Search ............ 8/405, 414, 415, 8/426, 428, 552, 580, 578, 597, 435

(56) References Cited

U.S. PATENT DOCUMENTS

| | | | |
|---|---|---|---|
| 3,337,411 A | * 8/1967 | Wilmsmann et al. | 8/406 |
| 3,977,826 A | * 8/1976 | Iscowitz | 8/406 |
| 4,132,793 A | * 1/1979 | Haber et al. | 426/250 |
| 4,268,264 A | * 5/1981 | Grollier et al. | 8/410 |
| 4,295,848 A | * 10/1981 | Grollier et al. | 8/421 |
| 4,314,807 A | * 2/1982 | Grollier et al. | 8/406 |
| 4,425,132 A | * 1/1984 | Grollier et al. | 8/405 |
| 4,566,875 A | * 1/1986 | Grollier et al. | 8/406 |
| 4,629,467 A | * 12/1986 | Clausen et al. | 8/414 |
| 4,865,774 A | 9/1989 | Fabry et al. | 252/554 |
| 4,931,218 A | 6/1990 | Schenker et al. | 252/551 |
| 5,042,988 A | 8/1991 | Anderson | 8/414 |
| 5,067,966 A | * 11/1991 | Mager et al. | 8/405 |
| 5,294,726 A | 3/1994 | Behler et al. | 554/98 |
| 5,560,750 A | * 10/1996 | Crews et al. | 8/431 |
| 5,817,155 A | * 10/1998 | Yasuda et al. | 8/406 |
| 5,843,193 A | * 12/1998 | Hawkins et al. | 8/408 |

FOREIGN PATENT DOCUMENTS

| | | |
|---|---|---|
| DE | 37 23 354 | 1/1989 |
| DE | 37 25 030 | 2/1989 |
| DE | 39 26 344 | 2/1991 |
| EP | 0 545 257 | 6/1993 |
| JP | 08 012 539 | 1/1996 |
| WO | WO 93/03706 | 3/1993 |

OTHER PUBLICATIONS

CAPLUS Abstract of JP 7–179,325, Ito Masatoshi, Jul. 1995.*
Derwent Patent Abstract (WPAT) of DE 3725030, 2/89.
Derwent Patent Abstract (WPAT) of DE 3723354, 01/89.
Derwent Patent Abstract (WPAT) of DE 3926344, 2/91.
Derwent Patent Abstract (WPAT) of JP8–12539, 01/96.
Chemical Abstracts 124 (18): 241753g, (Jan. 1996).
Derwent Patent Abstracts (WPAT) on DE 37 25 030, (Feb. 1989).
Derwent Patent Abstracts (WPAT) of DE 37 23 354, (Jan. 1989).
Derwent Patent Abstracts (WPAT) of DE 39 26 344, (Feb. 1991).
Derwent Patent Abstracts (WPAT) of JP 8–12539, (Jan. 1996).
Chemical Abstracts 124 (18): 241753g (Jan. 1996).
CAPLUS Abstract of JP 7–179,325, Ito Masatoshi, (Jul. 1995).

* cited by examiner

*Primary Examiner*—Margaret Einsmann
(74) *Attorney, Agent, or Firm*—Wayne Jaeschke; Kimberly R. Hild; Glenn E. J. Murphy

(57) ABSTRACT

Formulations for coloring keratinous fibers are provided, comprising a substantive dye, an aminopolycarboxylic acid or salt thereof with a physiologically compatible cation, and isoascorbic acid or a salt thereof with a physiologically compatible cation. Also provided are methods of coloring keratinous fibers with the formulations.

16 Claims, No Drawings

AGENT AND PROCESS FOR DYEING AND TINTING KERATINOUS FIBRES

CROSS REFERENCE TO RELATED APPLICATIONS

This application is a national stage application under 35 U.S.C. §371 of international application PCT/EP97/02280 filed May 5, 1997, the international application not being published in English.

BACKGROUND OF THE INVENTION

This invention relates to formulations for coloring and tinting keratin fibers, more particularly human hair, with a special combination of active substances.

Preparations for tinting and coloring hair are an important type of cosmetic product. They may be used to lighten or darken the natural hair color according to the wishes of the user, to obtain a totally different hair color or to cover unwanted hair colors, for example grey tones. Normal hair colorants are formulated either on the basis of oxidation dyes or on the basis of substantive dyes, depending on the required color and permanence. Combinations of oxidation dyes and substantive dyes are also used in many cases to obtain special shades.

Colorants based on oxidation dyes lead to brilliant and permanent color tones. However, they do involve the use of strong oxidizing agents, for example hydrogen peroxide solutions. This often causes damage to the hair to be colored which has to be counteracted with corresponding repair products. In addition, contact of the skin with these colorants can produce unwanted reactions in very sensitive people.

Colorants based on substantive dyes do not require oxidizing agents and can be better formulated at pH values in the vicinity of the neutral point. However, a major disadvantage of colorants based on substantive dyes is the poor fastness to washing of the colored hair. In many cases, the ability of the dye molecules to attach themselves to the hair and, in addition, the lustre of the colored hair are not entirely satisfactory.

Accordingly, there is still a need for colorants based on substantive dyes which are distinguished by improved absorption of the dye molecules onto the hair and/or by improved lustre of the colored hair.

It has now been found that the disadvantages mentioned above can be overcome to a surprisingly large extent and, in particular, the absorption of the dye molecules onto the hair and the lustre of the hair can be significantly improved with a combination of isoascorbic acid and special aminocarboxylic acids.

DESCRIPTION OF THE INVENTION

Accordingly, the present invention relates to a formulation for coloring or tinting keratin fibers, more particularly human hair, characterized in that, in addition to a substantive dye, it contains a combination of
- an aminopolycarboxylic acid or a salt thereof with a physiologically compatible cation and
- isoascorbic acid or a salt thereof with a physiologically compatible cation.

In the context of the invention, keratin fibers are understood to be pelts, wool, feathers and, in particular, human hair. Although the colorants according to the invention are mainly suitable for coloring keratin fibers, there is nothing in principle to stop them being used in other fields.

The active-substance combination according to the invention consists of two compulsory components.

The first component is an aminopolycarboxylic acid. An aminopolycarboxylic acid is a compound which contains at least one optionally substituted amino group and at least two carboxylic acid groups. Aminopolycarboxylic acids capable of forming chelate complexes have proved to be particularly suitable.

According to the invention, preferred aminopolycarboxylic acids are nitrilotriacetic acid, ethylenediamine tetraacetic acid, diethylenetriamine pentaacetic acid and N-hydroxyethyl ethylenediamine triacetic acid. Of these compounds, ethylenediamine tetraacetic acid is particularly preferred.

The aminopolycarboxylic acids may be added to the formulations according to the invention as free acids. However, the aminopolycarboxylic acids may also be added in the form of salts with physiologically compatible cations. Such cations are, for example, alkali metal, alkaline earth metal, aluminium, ammonium and mono-, di- and trialkanolammonium ions. Alkali metal ions, particularly sodium ions, are preferred ions.

The disodium salt and, in particular, the tetrasodium salt of ethylenediamine tetraacetic acid has proved to be an eminently suitable component of the active-substance combination according to the invention.

The formulations according to the invention contain the aminopolycarboxylic acid or its salt in a quantity of preferably 0.01 to 1% by weight, based on the formulation as a whole. Quantities of 0.05 to 0.5% by weight are particularly preferred.

The second compulsory component of the active-substance combination according to the invention is isoascorbic acid or a salt thereof with a physiologically compatible cation.

The formulations according to the invention contain isoascorbic acid in a quantity of preferably 0.01 to 1% by weight, based on the formulation as a whole. Quantities of 0.05 to 0.5% by weight are particularly preferred.

The formulations according to the invention produced particularly favorable results when the quantity ratios (=ratios by weight) of aminopolycarboxylic acid and isoascorbic acid were between 2:1 and 1:2.

In addition, the formulations according to the invention contain at least one substantive dye. The substantive dye is normally selected from the group of nitrilophenylenediamines, nitroaminophenols, anthraquinones or indophenols. Corresponding compounds are, for example, the compounds known under the International names or commercial names of HC Yellow 2, HC Yellow 4, Basic Yellow 57, Disperse Orange 3, HC Red 3, HC Red BN, Basic Red 76, HC Blue 2, Disperse Blue 3, Basic Blue 99, HC Violet 1, Disperse Violet 1, Disperse Violet 4, Disperse Black 9, Basic Brown 16, picramic acid and Rodol 9 R and also 4-amino-2-nitrodiphenylamine-2'-carboxylic acid, 6-nitro-1,2,3,4-tetrahydroquinoxaline, (N-2,3-dihydroxypropyl-2-nitro-4-trifluoromethyl)-aminobenzene and 4-N-ethyl-1,4-bis-(2'-hydroxy-ethylamino)-2-nitrobenzene hydrochloride. In the context of the invention, substantive dyes also include naturally occurring dyes such as, for example, henna red, henna neutral, henna black, camomile blossom, sandalwood, black tea, black alder bark, sage, logwood, madder root, catechu, sedre and alkanet.

The substantive dyes are present in the formulations according to the invention in quantities of preferably 0.01 to 20% by weight, based on the formulation as a whole.

The formulations according to the invention may also contain oxidation dye precursors, so-called primary intermediates and secondary intermediates. The primary intermediates form the actual dyes with one another under the influence of oxidizing agents or atmospheric oxygen, optionally with the aid of special enzymes, or by coupling with one or more secondary intermediates.

The primary intermediates normally used are primary aromatic amines containing another free or substituted hydroxy or amino group in the para or ortho position, diaminopyridine derivatives, heterocyclic hydrazones, 4-aminopyrazolone derivatives and 2,4,5,6-tetraaminopyrimidine and derivatives thereof. Special representatives are, for example, p-phenylenediamine, p-toluylenediamine, 2,4,5,6-tetraaminopyrimidine, p-aminophenol, N,N-bis-(2-hydroxyethyl)-p-phenylenediamine, 2-(2,5-diaminophenoxy)-ethanol, 2-(2,5-diaminophenoxy)-ethanol, 1-phenyl-3-carboxyamido-4-amino-5-pyrazolone, 4-amino-3-methylphenol, 2-aminomethyl-4-aminphenol, 2-hydroxymethyl-4-aminophenol, 4-amino-2-(2-hydroxyethoxy)-phenol, 4-hydroxy-2,5,6-triaminopyrimidine, 2-hydroxy-4,5,6-triaminopyrimidine, 2,4-hydroxy-5,6-diaminopyrimidine and 2,5,6-triaminohydroxypyrimidine.

The secondary intermediates are generally m-phenylenediamine derivatives, naphthols, resorcinol and resorcinol derivatives, pyrazolones and m-aminophenols. Particularly suitable secondary intermediates are α-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)-propane, 2-chlororesorcinol, 4-chlororesorcinol, 2-chloro-6-methyl-3-aminophenol, 2-amino-4-hydroxypyridine, 2-methyl resorcinol and 5-methyl resorcinol.

According to the invention, preferred primary and secondary intermediates are those which do not require any oxidizing agents apart from atmospheric oxygen to form the colors.

The primary and secondary intermediates are normally used in free form. However, in cases where compounds containing amino groups are used, it may be preferred to use them in salt form, more particularly in the form of the hydrochlorides and sulfates.

The hair colorants according to the invention contain both the primary intermediates and the secondary intermediates in a quantity of preferably 0.005 to 20% by weight and more preferably 0.1 to 5% by weight, based on the oxidation colorant as a whole. The primary and secondary intermediates are generally used in a substantially equimolar ratio to one another. Although it has proved to be useful to employ the primary and secondary intermediates in an equimolar ratio, a certain excess of individual oxidation dye precursors is by no means a disadvantage, so that the primary and secondary intermediates may be present in a molar ratio of 1:0.5 to 1:2.

So far as other typical dye components are concerned, reference is expressly made to the Colipa list published by the Industrieverband Körperpflege und Waschmittel, Frankfurt.

The oxidation dye precursors or the substantive dyes optionally present do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

The effects obtained by the formulations according to the invention may be enhanced by including a $C_{8-18}$ carboxylic acid in the formulations in addition to the two compulsory components of the active-substance combination.

In principle, both saturated and mono- or polyunsaturated, linear or branched carboxylic acids may be used providing the consistency of the required formulation allows. However, saturated carboxylic acids containing 10 to 18 carbon atoms have proved to be particularly effective. Accordingly, myristic acid, palmitic acid and, in particular, lauric acid are particularly preferred other components of the formulations according to the invention.

Another component which has an advantageous effect on the properties of the formulations according to the invention are oligomeric and polymeric polyols. Preferred compounds are polyethylene glycols, polypropylene glycols and polyglycerols. Of these polyols, polyethylene glycols are particularly preferred. These polyols preferably have a molecular weight of 500 to 3,000 dalton. Molecular weights of 1,000 to 2,000 dalton and, more particularly, of the order of 1,500 dalton are particularly preferred.

To produce the colorants according to the invention, the oxidation dye precursors are incorporated in a suitable water-containing carrier. For coloring hair, such carriers are, for example, cremes, emulsions, gels or even surfactant-containing foaming solutions, for example shampoos, foam aerosols or other formulations suitable for application to the hair.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants. Anionic surfactants can be particularly useful.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ether, amide and hydroxyl groups and—generally—ester groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear and branched fatty acids containing 8 to 22 carbon atoms (soaps), ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O(CH$_2$—CH$_2$O)$_x$—OSO$_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated C$_{8-22}$ carboxylic acids, such as oleic acid, stearic acid, isostearic acid and palmitic acid.

In the context of the invention, zwitterionic surfactants are surface-active active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a C$_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and C$_{12-18}$ acyl sarcosine.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group, C$_{12-22}$ fatty acid monoesters and diesters of products of the addition of 1 to 30 moles of ethylene oxide to glycerol, C$_{8-22}$ alkyl mono- and oligoglycosides and ethoxylated analogs thereof, products of the addition of 5 to 60 moles of ethylene oxide to castor oil and hydrogenated castor oil, products of the addition of ethylene oxide to sorbitan fatty acid esters, products of the addition of ethylene oxide to fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the dialkyl ammonium methosulfates and methyl hydroxyalkyl dialkoyloxyalkyl ammonium methosulfates marketed under the trade name of Stepantex® are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example,

- nonionic polymers such as, for example, vinyl pyrrolidone/vinyl acrylate copolymers, polyvinyl pyrrolidone and vinyl pyrrolidone/vinyl acetate copolymers and polysiloxanes,
- cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol,
- zwitterionic and amphoteric polymers such as, for example, acrylamido-propyl/trimethyl ammonium chloride/acrylate copolymers and octyl acrylamide/methyl methacrylate/tert.butyl aminoethyl methacrylate/2-hydroxypropyl methacrylate copolymers,
- anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers,
- thickeners, such as agar agar, guar gum, alginates, xanthan gum, gum arabic, karaya gum, carob bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol,
- structurants, such as glucose, maleic acid and lactic acid,
- hair-conditioning compounds, such as phospholipids, for example soya lecithin, egg lecithin and kephalins, and also silicone oils,
- protein hydrolyzates, more particularly elastin, collagen, keratin, milk protein, soya protein and wheat protein hydrolyzates, condensation products thereof with fatty acids and quaternized protein hydrolyzates,
- perfume oils, dimethyl isosorbide and cyclodextrins,
- solubilizers, such as ethanol, isopropanol, ethylene glycol, propylene glycol, glycerol and diethylene glycol,
- dyes for coloring the formulations,
- antidandruff agents, such as Piroctone Olamine and Zinc Omadine,
- other substances for adjusting the pH value,
- active substances, such as panthenol, pantothenic acid, allantoin, pyrrolidone carboxylic acids and salts thereof, plant extracts and vitamins,
- cholesterol,
- UV filters,
- consistency promoters, such as sugar esters, polyol esters or polyol alkyl ethers,
- fats and waxes, such as spermaceti, beeswax, montan wax, paraffins, fatty alcohols and fatty acid esters,
- fatty acid alkanolamides,
- complexing agents, such as phosphonic acids,
- swelling and penetration agents, such as glycerol, propylene glycol monoethyl ether, carbonates, hydrogen carbonates, guanidines, ureas and primary, secondary and tertiary phosphates,
- opacifiers, such as latex,
- pearlescers, such as ethylene glycol mono- and distearate,
- propellents, such as propane/butane mixtures, $N_2O$, dimethyl ether, $CO_2$ and air and
- antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

The present invention also relates to the use of a formulation according to the invention for coloring and tinting keratin fibers, particularly human hair.

Although the preparations according to the invention can be formulated to stay on the hair, they are preferably formulated as wash-off preparations.

Accordingly, the present invention also relates to a process for coloring and tinting keratin fibers, more particularly human hair, in which a formulation according to the invention is applied to the hair, left thereon for about 1 minute to 1 hour and then rinsed off.

The following Examples are intended to illustrate the invention.

EXAMPLES

All quantities in the Examples are in parts by weight.

| 1. Coloring lotion | |
|---|---|
| $C_{12-18}$ Fatty alcohol | 3.00 |
| Emulgade ® 1000 NI[1] | 2.00 |
| Lauric acid | 3.00 |
| Texapon ® N 70[2] | 3.00 |
| Dehyton ® K[3] | 3.00 |
| Paridol ® M[4] | 0.20 |
| Paridol ® P[5] | 0.20 |
| Isoascorbic acid | 0.10 |
| Trilon ® B[6] | 0.25 |
| 2-Amino-2-methyl propanol | 0.70 |
| HC Blue 2[7] | 0.70 |
| Violet 1, 4 D[8] | 0.30 |
| HC Yellow 2[9] | 0.40 |
| Fragrances | 0.30 |
| Water dist. to | 100 |

[1] nonionic cetyl stearyl alcohol/emulsifier mixture (INCI name: Cetearyl Alcohol (and) Ceteareth-20) (HENKEL)
[2] sodium lauryl ether sulfate (ca. 72% active substance in water; INCI name: Sodium Laureth Sulfate) (HENKEL)
[3] fatty acid amide derivative of betaine structure with the formula R—CONH—$(CH_2)_3$—$N^+(CH_3)_2CH_2COO^-$ (ca. 30% active substance in water; INCI name: Cocamidopropyl Betaine) (HENKEL)
[4] 4-hydroxybenzoic acid methyl ester (INCI name: Methylparaben) (NAAR-DEN)
[5] 4-hydroxybenzoic acid propyl ester (INCI name: Propylparaben) NAAR-DEN)
[6] ethylenediamine tetraacetic acid tetrasodium salt (40% active substance in water, INCI name: Tetrasodium-EDTA) (BASF)
[7] N,N,N'-tris-(2-hydroxyethyl)-2-nitro-1,4-phenylenediamine (GRAFOX)
[8] N,N'-bis-(2-hydroxyethyl)-2-nitro-1,4-phenylenediamine (GRAFOX)
[9] 1-(2-hydroxyethylamino)-2-nitrobenzene (GRAFOX)

The coloring lotion had a pH value of 7-

| 2. Coloring lotion | |
|---|---|
| $C_{12-18}$ Fatty alcohol | 3.00 |
| Emulgade ® 1000 NI | 2.00 |
| Lauric acid | 3.00 |
| Texapon ® N 70 | 3.00 |
| Dehyton ® K | 3.00 |
| Lutrol ® E 1500[10] | 1.00 |
| Paridol ® M | 0.20 |
| Paridol ® P | 0.20 |
| Isoascorbic acid | 0.10 |
| Trilon ® B | 0.25 |
| 2-Amino-2-methyl propanol | 0.70 |
| HC Blue 2 | 1.50 |
| HC Red 3[11] | 0.10 |
| Rodol 9 R[12] | 0.10 |
| HC Yellow 2 | 0.15 |
| Diethylene glycol monoethyl ether | 3.00 |
| Fragrances | 0.30 |
| Water dist. to | 100 |

[10]polyethylene glycol (INCL name: PEG 32) (BASF)
[11]N-(2-hydroxyethyl)-2-nitro-1,4-phenylenediamine (GRAFOX)
[12]6-Chloro-4-nitro-2-aminophenol (LOWENSTEIN)

The coloring lotion had a pH value of 7.

What is claimed is:

1. A formulation for coloring keratinous fibers comprising
    (a) a substantive dye, in an amount effective to dye keratinous fibers;
    (b) an aminopolyearboxylic acid or salt thereof with a physiologically compatible cation;
    (c) isoascorbic acid or a salt thereof with a physiologically compatible cation;
    (d) a $C_8$ to $C_{18}$ carboxylic acid; and
    (e) an oligomeric or polymeric polyol selected from polyethylene glycol, polypropylene glycol, or polyglycerol, or combinations thereof.

2. A formulation according to claim 1, wherein the aminopolycarboxylic acid is selected from the group consisting of nitrilotriacetic acid, ethylenediamine tetraacetic acid, diethylenetriamine pentaacetic acid, N-hydroxy-ethyl ethylenediamine triacetic acid and salts thereof with a physiologically compatible cation.

3. A formulation according to claim 2, wherein the aminopolycarboxlic acid is ethylenediamine tetraacetic acid or a salt thereof with a physiologically compatible cation.

4. A formulation according to claim 1, wherein the salt of the aminopolycarboxlic acid is an alkali metal, alkaline earth metal, aluminum, ammonium, or mono-, di-, or trialkanolammonium salt thereof.

5. A formulation according to claim 4, wherein the salt is the di- or tetrasodium salt of ethylenediamine tetraacetic acid.

6. A formulation according to claim 1, wherein the carboxylic acid is a saturated $C_{10}$ to $C_{18}$ carboxylic acid.

7. A formulation according to claim 6, wherein the carboxylic acid is lauric acid.

8. A formulation according to claim 1, wherein the polyol comprises polyethylene glycol having a molecular weight of 500 daltons to 3,000 daltons.

9. A formulation according to claim 1, wherein the aminopolycarboxylic acid or its salt is present in a quantity of 0.01% by weight to 1% by weight, based on the total weight of the formulation.

10. A formulation according to claim 1, wherein the isoascorbic acid or its salt is present in a quantity of 0.01% by weight to 1% by weight, based on the total weight of the formulation.

11. A process for coloring keratinous fibers comprising the steps of contacting a keratinous fiber with the formulation of claim 1 for about 1 minute to about 1 hour and rinsing the formulation from the fiber.

12. A formulation for coloring keratinous fibers comprising
    (a) a substantive dye, in an amount effective to dye keratinous fibers;
    (b) from 0.01% by weight to 1% by weight, based on the total weight of the formulation, of an aminopolycarboxylic acid or salt thereof with a physiologically compatible cation, wherein the aminopolycarboxylic acid is selected from the group consisting of nitrilotriacetic acid, ethylenediamine tetraacetic acid, diethylenetriamine pentaacetic acid, N-hydroxy-ethyl ethylenediamine triacetic acid, and salts thereof with a physiologically compatible cation;
    (c) from 0.01% by weight to 1% by weight, based on the total weight of the formulation, of an isoascorbic acid or a salt thereof with a physiologically compatible cation;
    (d) a $C_8$ to $C_{18}$ carboxylic acid; and
    (e) an oligomeric or polymeric polyol selected from polyethylene glycol, polypropylene glycol, or polyglycerol, or combinations thereof.

13. A formulation according to claim 12, wherein the carboxylic acid is a saturated $C_{10}$ to $C_{18}$ carboxylic acid.

14. A method of increasing the absorption of a substantive dye onto keratinous fibers or increasing the luster of keratinous fibers colored with a substantive dye comprising:
    (a) forming a composition comprising
        (i) a substantive dye, in an amount effective to dye keratinous fibers;
        (ii) an aminopolycarboxylic acid or salt thereof with a physiologically compatible cation;
        (iii) isoascorbic acid or a salt thereof with a physiologically compatible cation,
        (iv) a $C_8$ to $C_{18}$ carboxylic acid; and
        (v) an oligomeric or polymeric polyol selected from polyethylene glycol, polypropylene glycol, or polyglycerol, or combinations thereof; and
    (b) applying the composition to keratinous fibers to color the keratinous fibers, wherein the composition increases the absorption of the substantive dye on the fibers or increases the luster of the colored keratinous fibers, or both.

15. A method according to claim 14, wherein the carboxylic acid is a saturated $C_{10}$ to $C_{18}$ carboxylic acid.

16. A method according to claim 15, wherein the aminopolycarboxylic acid is selected from the group consisting of nitrilotriacetic acid, ethylenediamine tetraacetic acid, diethylenetriamine pentaacetic acid, N-hydroxy-ethyl ethylenediamine triacetic acid and salts thereof with a physiologically compatible cation.

* * * * *